US008961970B2

(12) United States Patent
Huang et al.

(10) Patent No.: US 8,961,970 B2
(45) Date of Patent: Feb. 24, 2015

(54) COMBINATION THERAPY

(71) Applicants: Xizhong Huang, Southborough, MA (US); Malte Peters, Basel (CH); Jennifer Lorraine Gansert, Simi Valley, CA (US); David Dong Eun Chang, Calabasas, CA (US); Pedro Beltran, Thousand Oaks, CA (US); Zhu Alexander Cao, Acton, MA (US)

(72) Inventors: Xizhong Huang, Southborough, MA (US); Malte Peters, Basel (CH); Jennifer Lorraine Gansert, Simi Valley, CA (US); David Dong Eun Chang, Calabasas, CA (US); Pedro Beltran, Thousand Oaks, CA (US); Zhu Alexander Cao, Acton, MA (US)

(73) Assignees: Novartis AG, Basel (CH); Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/799,706

(22) Filed: Mar. 13, 2013

(65) Prior Publication Data
US 2013/0273061 A1 Oct. 17, 2013

Related U.S. Application Data

(60) Provisional application No. 61/613,046, filed on Mar. 20, 2012, provisional application No. 61/763,767, filed on Feb. 12, 2013.

(51) Int. Cl.
*A61K 39/395* (2006.01)
*C07K 16/28* (2006.01)
*A61K 31/4184* (2006.01)
*A61K 39/00* (2006.01)

(52) U.S. Cl.
CPC ......... *A61K 39/3955* (2013.01); *C07K 16/2863* (2013.01); *A61K 31/4184* (2013.01); *A61K 2039/545* (2013.01)
USPC .................................................... 424/133.1

(58) Field of Classification Search
None
See application file for complete search history.

(56) References Cited

U.S. PATENT DOCUMENTS 7,871,611 B2   1/2011   Calzone et al.

FOREIGN PATENT DOCUMENTS

| WO | WO 03/077914 A1 | 9/2003 |
| WO | WO 2005/094376 A2 | 10/2005 |
| WO | WO 2006/069202 A2 | 6/2006 |
| WO | WO 2008/106168 A1 | 9/2008 |
| WO | WO 2008/108986 A2 | 9/2008 |
| WO | 2012/106556 * | 8/2012 |

OTHER PUBLICATIONS

Strome et al., The Oncologist, 2007; 12:1084-95.*
Brand et al., Anticancer Res. 2006; 26:463-70.*
Yeh et al, Clinical Cancer Research vol. 13 p. 1576 (2007).*
U.S. National Institutes of Health: A Study of MEK162 and AMG 479 in Patients With Selected Solid Tumors; Mar. 22, 2012, XP002711623, URL: http://clinicaltrials.gov/show/NCT01562899, 4 pages.
International Search Report and Written Opinion, PCT/US2013/030781, dated Sep. 2013, 14 pages.

* cited by examiner

*Primary Examiner* — Sheela J Huff
(74) *Attorney, Agent, or Firm* — Lathrop & Gage LLP; Brian C. Trinque

(57) ABSTRACT

The present invention relates to a pharmaceutical combination comprising a MEK inhibitor compound 6-(4-bromo-2-fluorophenylamino)-7-fluoro-3-methyl-3H-benzoimidazole-5-carboxylic acid (2-hydroxyethyoxy)-amide or a pharmaceutically acceptable salt thereof and the IGF1R inhibitor ANTIBODY A, a pharmaceutical composition comprising such combination, methods for treating cancer comprising administration of a therapeutically effective amount of such combination to a subject in need thereof, and uses of such combination for the treatment of cancer.

10 Claims, 1 Drawing Sheet

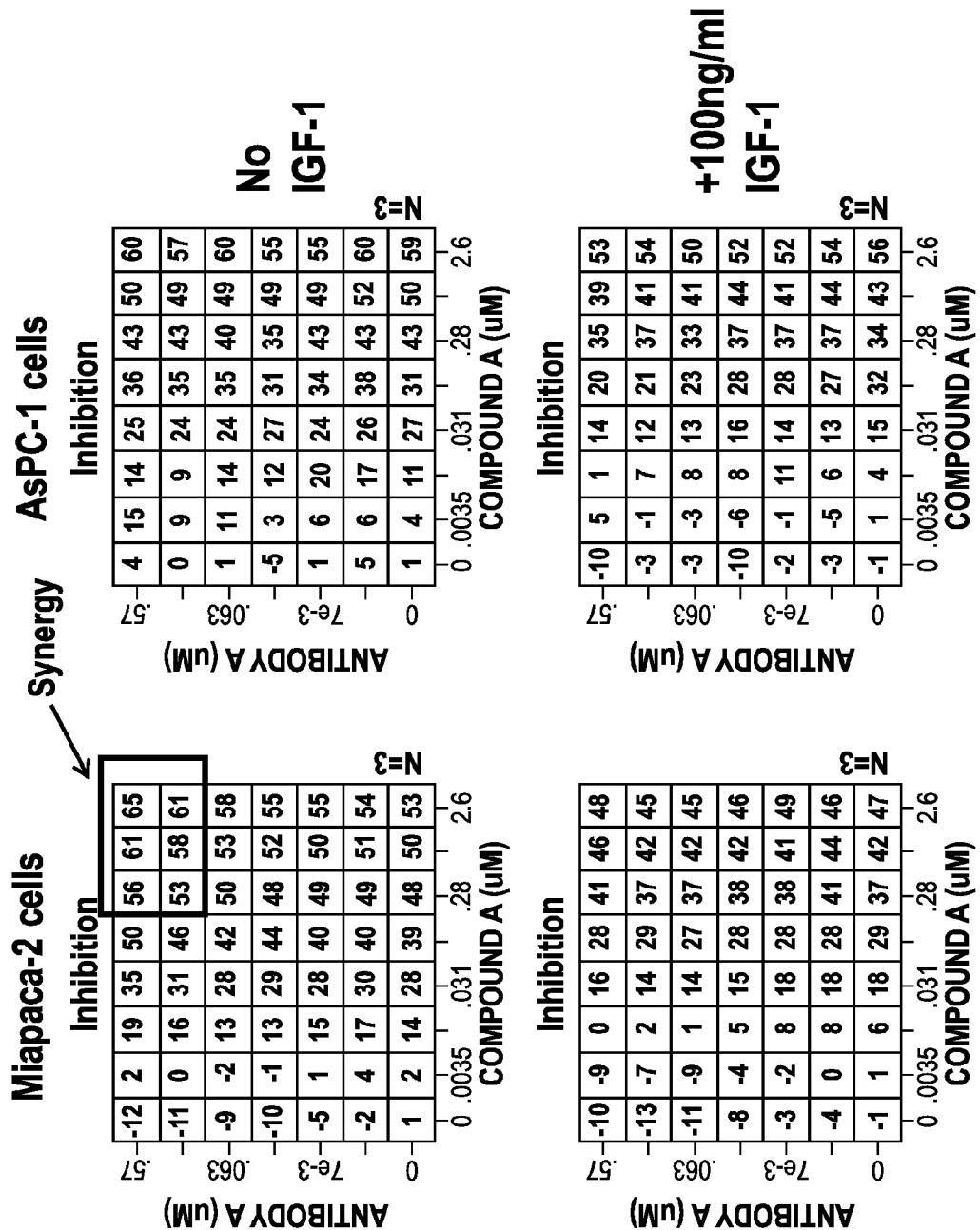

COMBINATION THERAPY

RELATED APPLICATIONS

This application claims priority to U.S. Provisional Application Ser. No. 61/613,046, filed Mar. 20, 2012, and U.S. Provisional Application Ser. No. 61/763,767, filed Feb. 12, 2013, which are both incorporated herein by reference in their entireties.

FIELD OF THE INVENTION

The present invention relates to a pharmaceutical combination comprising the MEK inhibitor compound 6-(4-bromo-2-fluorophenylamino)-7-fluoro-3-methyl-3H-benzoimidazole-5-carboxylic acid (2-hydroxyethyoxy)-amide or a pharmaceutically acceptable salt thereof and the IGF1R inhibitor ANTIBODY A, a pharmaceutical composition comprising such combination; methods for treating cancer comprising administration of a therapeutically effective amount of such combination to a subject in need thereof, and uses of such combination for the treatment of cancer.

BACKGROUND OF THE INVENTION

The RAS/RAF/MEK/ERK pathway is involved in growth factor-mediated proliferative signaling. This pathway comprises an evolutionarily conserved signaling cascade activated by the RAS small guanidine triphosphatase (GTPase), which in turn activates RAF, which in turn phosphorylates and activates MEK, and which in turn activates extracellular signal-regulated kinase (ERK). ERK-mediated phosphorylation of a variety of transcriptional factors regulates several key cellular activities including proliferation, differentiation, migration, survival and angiogenesis.

Aberrant signaling through the RAS/RAF/MEK/ERK pathway leads to unconstrained cell growth and cell transformation and is a characteristic feature of many cancers. Inappropriate activation of the RAS pathway can occur through several distinct mechanisms, including activating mutations in KRAS, activating mutations in NRAS, and the serine/threonine kinase BRAF. Approximately 15% of human cancers carry activating RAS mutations, including colorectal cancer (CRC) (40% KRAS mutations), pancreatic cancer (KRAS 70-90% mutations) and non-small cell lung cancer (NSCLC) (30% KRAS mutations). Activating mutations in BRAF occur in 7-8% of all solid tumors and in 60% of malignant melanomas, 8-15% of CRC and 3% of cases of pancreatic carcinoma. Somatic mutations in BRAF and NRAS occur in 50-60% and 15-20% of cutaneous melanomas respectively. In general, such activating mutations of KRAS, NRAS and BRAF are considered to be critical promoters of malignancy.

Further, insulin-like growth factor-1 receptor (IGF1R), a transmembrane tyrosine kinase, is widely expressed on normal tissues. The receptor is activated by binding of the natural ligands IGF1 and IGF2 and leads to activation of the PI3K/AKT and the RAS/RAF/MEK/ERK pathway. Signaling through the phosphatidylinositol 3' kinases (PI3K) regulates diverse cellular functions, including protein synthesis and glucose metabolism, cell survival and growth, proliferation, cellular resilience and repair, cell migration, and angiogenesis. Upon activation, PI3K generates PIP3, a lipid "second messenger", which in turn activates AKT (PKB), a serine/threonine kinase which is probably the best understood downstream effector of PI3K. The PI3K signaling is negatively regulated by action of dual specificity protein phosphatases/3-PI phosphatases, namely the tumor suppressor PTEN.

Activation of the PI3K/AKT pathway associated with increased IGF1R signaling is known to occur in various cancer types, such as pancreatic carcinoma, colorectal cancer and melanoma. IGF1R is often found to be overexpressed by cancer cell lines and human cancers, and many cancer cell lines are mitogenically responsive to physiological concentrations of IGFs. IGF1R overexpression, however, in contrast to other receptor tyrosine kinase receptors, does not appear to be associated with gene amplification or gene mutation. IGF1R is found to establish resistance to epidermal growth factor receptor (EGFR) inhibitors in EGFR amplified tumors by loss of insulin-growth factor binding protein expression.

Many cancers, particularly those carrying EGFR amplifications, KRAS-mutations, or BRAF-mutations are amenable to treatment with epidermal growth factor receptor (EGFR) inhibitors, IGF1R inhibitors and/or BRAF-inhibitors, respectively. However, in many cases these cancers acquire resistance to these chosen therapeutic and ultimately become refractory to treatment.

In spite of numerous treatment options for cancer patients, there remains a need for effective and safe therapeutic agents and a need for their preferential use in combination therapy. In particular, there is a need in the art for novel methods of treating cancers, particularly those carrying EGFR amplification, EGFR activating mutations, IGF1R activating signature (e.g., overexpression of IGF1R, high circulating levels of IGF-1, or high levels of IGFBP1), KRAS-mutant, NRAS-mutant or BRAF-mutated cancers, especially those cancers that have been resistant and/or refractive to current therapies.

SUMMARY OF THE INVENTION

The present invention relates in part to a pharmaceutical combination comprising (a) the compound 6-(4-bromo-2-fluorophenylamino)-7-fluoro-3-methyl-3H-benzoimidazole-5-carboxylic acid (2-hydroxyethyoxy)-amide (COMPOUND A) or a pharmaceutically acceptable salt thereof, and (b) the IGF1R inhibitor, ANTIBODY A, comprising the heavy chain amino acid sequence set forth in SEQ ID NO:1 and the light chain amino acid sequence set forth in SEQ ID NO:2, herein.

In one embodiment, the present invention comprises a pharmaceutical combination comprising the compound 6-(4-bromo-2-fluorophenylamino)-7-fluoro-3-methyl-3H-benzoimidazole-5-carboxylic acid (2-hydroxyethyoxy)-amide or a pharmaceutically acceptable salt thereof and the IGF1R inhibitor ANTIBODY A for use in the treatment of cancer in a subject in need thereof. The combination of the present invention can be used to treat subjects suffering from, for example, cancers having EGFR amplification, EGFR activating mutations, IGF1R activating signature (e.g., overexpression of IGF1R, high circulating levels of IGF-1, or high levels of IGFBP1), KRAS-mutations, NRAS-mutations and BRAF-mutations. Suitable cancers include, without limitation, pancreatic cancer, e.g., locally advanced pancreatic cancer and KRAS-mutated pancreatic cancer.

In a further embodiment, the present invention comprises a pharmaceutical combination comprising the compound 6-(4-bromo-2-fluorophenylamino)-7-fluoro-3-methyl-3H-benzoimidazole-5-carboxylic acid (2-hydroxyethyoxy)-amide or a pharmaceutically acceptable salt thereof and the IGF1R inhibitor ANTIBODY A for use in the treatment of cancers that are resistant or refractive to currently-available therapies, e.g., EGFR amplified, KRAS-mutated cancers, NRAS-mutant and BRAF-mutated cancers that a resistant or refractive to EGFR inhibitors, IGF1R inhibitors, or BRAF inhibitors, in a subject in need thereof.

In a further embodiment, the present invention comprises the combination of 6-(4-bromo-2-fluorophenylamino)-7-fluoro-3-methyl-3H-benzoimidazole-5-carboxylic acid (2-hydroxyethyoxy)-amide (COMPOUND A) or a pharmaceutically acceptable salt thereof and ANTIBODY A displaying a synergistic effect.

The present invention provides a method of treating cancer in a subject (e.g., patient) by administering to the subject in need of such treatment a therapeutically effective amount or dose of a combination of COMPOUND A or a pharmaceutically acceptable salt thereof and ANTIBODY A.

In one embodiment, the present invention provides a method of treating cancer by administering to subject in need of such treatment a quantity of COMPOUND A or pharmaceutically acceptable salt thereof and ANTIBODY A which is jointly therapeutically effective for said treatment.

In a further embodiment, COMPOUND A and ANTIBODY A are in a single formulation or unit dosage form. In a further embodiment, COMPOUND A and ANTIBODY A are in separate formulations or unit dosage forms.

In a further embodiment, COMPOUND A and/or ANTIBODY A are administered at substantially the same time. In a further embodiment, COMPOUND A and/or ANTIBODY A are administered at different times. In a further embodiment, COMPOUND A is administered to the subject prior to administration of ANTIBODY A. In a further embodiment, ANTIBODY A is administered to the subject prior to administration of COMPOUND A.

In a further embodiment, COMPOUND A is administered at a dosage of between about 15 and 60 mg, e.g., between 15 and 60 mg. In a further embodiment, MONOCLONAL ANTIBODY A is administered at a dosage of between about 9 and 20 mg/kg, e.g., between 9 and 20 mg/kg.

The present invention provides a method for treating a cancer that is resistant or refractive to prior treatment with an EGFR modulator, IGF1R inhibitor, or BRAF inhibitor comprising administering a therapeutically effective amount of COMPOUND A or a pharmaceutically acceptable salt thereof and ANTIBODY A to a subject in need thereof.

The present invention further provides a method for the treatment of cancer that is resistant or refractive to treatment with the IGF1R inhibitor ANTIBODY A by administering a therapeutically effective amount of COMPOUND A or a pharmaceutically acceptable salt thereof.

The present invention provides a use of the pharmaceutical combination comprising COMPOUND A or a pharmaceutically acceptable salt thereof and ANTIBODY A for the manufacture of a pharmaceutical preparation or medicament for the treatment of cancer.

The present invention further provides the use of a pharmaceutical combination comprising COMPOUND A or a pharmaceutically acceptable salt thereof and ANTIBODY A for the manufacture of a pharmaceutical preparation or medicament for the treatment of cancer that is resistant or refractive to treatment with an EGFR modulator, IGF1R inhibitor, or BRAF inhibitor.

The present invention further provides the use of COMPOUND A or a pharmaceutically acceptable salt thereof for the treatment of cancer that is resistant or refractive to treatment with the IGF1R inhibitor ANTIBODY A.

In one embodiment, the present invention relates to a pharmaceutical composition or pharmaceutical formulation comprising (a) COMPOUND A or a pharmaceutically acceptable salt thereof, and (b) ANTIBODY A, and optionally one or more pharmaceutically acceptable carriers.

In a further embodiment, the present invention further relates to a pharmaceutical composition or pharmaceutical formulation comprising (a) COMPOUND A or a pharmaceutically acceptable salt thereof, and (b) ANTIBODY A, and optionally one or more pharmaceutically acceptable carriers, for use in the treatment of cancer.

In a further embodiment, the present invention relates to (a) a pharmaceutical combination comprising COMPOUND A or a pharmaceutically acceptable salt thereof, and (b) a pharmaceutical composition comprising ANTIBODY A administered in separate pharmaceutical compositions to a subject in need thereof.

BRIEF DESCRIPTION OF THE DRAWINGS

FIG. 1 depicts the results of experiments to determine the effect of the combination of COMPOUND A and ANTIBODY A on Miapaca-2 and AsPC-1 cell proliferation in the absence or presence of 100 ng/ml IGF1.

DETAILED DESCRIPTION OF THE INVENTION

The present invention relates to a pharmaceutical combination comprising the compound 6-(4-bromo-2-fluorophenylamino)-7-fluoro-3-methyl-3H-benzoimidazole-5-carboxylic acid (2-hydroxyethyoxy)-amide (COMPOUND A) or a pharmaceutically acceptable salt thereof and the IGF1R inhibitor ANTIBODY A.

Certain terms used herein are described below. Compounds and antibodies of the present invention are described using standard nomenclature. Unless defined otherwise, all technical and scientific terms used herein have the same meaning as is commonly understood by one of skill in the art to which this invention belongs.

The term "pharmaceutical combination" as used herein refers to either a fixed combination in one dosage unit form, or non-fixed combination or a kit of parts for the combined administration where two or more therapeutic agents can be administered independently at the same time or separately within time intervals, especially where these time intervals allow that the combination partners show a cooperative, e.g. synergistic effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, or in separate containers (e.g., capsules and/or intravenous formulations) for each active ingredient. In addition, such administration also encompasses use of each type of therapeutic agent in a sequential manner, either at approximately the same time or at different times. In either case, the treatment regimen will provide beneficial effects of the drug combination in treating the conditions or disorders described herein.

The term "MEK inhibitor" as used herein refers to a compound that targets, decreases or inhibits at least one activity of a MEK serine kinase. Exemplary MEK inhibitors are disclosed in International PCT Application WO2003/0077914, which is hereby incorporated by reference in its entirety.

The term "IGF1R inhibitor" as used herein refers to a compound that targets, decreases, or inhibits at least one activity of an Insulin Growth Factor-1 Receptor. Exemplary IGF1R inhibitors are disclosed in U.S. Pat. No. 7,871,611, which is hereby incorporated by reference in its entirety.

The term "pharmaceutically acceptable" as used herein refers to those compounds, antibodies, materials, compositions and/or dosage forms, which are, within the scope of sound medical judgment, suitable for contact with the tissues a warm-blooded animal, e.g., a mammal or human, without excessive toxicity, irritation allergic response and other problem complications commensurate with a reasonable benefit/risk ratio.

The terms "fixed combination", "fixed dose" and "single formulation" as used herein refers to a single carrier or vehicle or dosage form formulated to deliver an amount, which is jointly therapeutically effective for the treatment of cancer, of both therapeutic agents to a patient. The single vehicle is designed to deliver an amount of each of the agents, along with any pharmaceutically acceptable carriers or excipients. In some embodiments, the vehicle is a tablet, capsule, pill, or a patch. In other embodiments, the vehicle is a solution or a suspension.

The term "non-fixed combination" or "kit of parts" means that the active ingredients, e.g. COMPOUND A and ANTIBODY A, are both administered to a patient as separate entities either simultaneously, concurrently or sequentially with no specific time limits, wherein such administration provides therapeutically effective levels of the two compounds in the body of the warm-blooded animal in need thereof. The latter also applies to cocktail therapy, e.g., the administration of three or more active ingredients.

The term "unit dose" is used herein to mean simultaneous administration of both agents together, in one dosage form, to the patient being treated. In some embodiments, the unit dose is a single formulation. In certain embodiments, the unit dose includes one or more vehicles such that each vehicle includes an effective amount of at least one of the agents along with pharmaceutically acceptable carriers and excipients. In some embodiments, the unit dose is one or more tablets, capsules, pills, or patches administered to the patient at the same time.

An "oral dosage form" includes a unit dosage form prescribed or intended for oral administration.

The term "treat" is used herein to mean to relieve, reduce or alleviate, at least one symptom of a disease in a subject. Within the meaning of the present invention, the term "treat" also denotes, to arrest, delay the onset (i.e., the period prior to clinical manifestation of a disease or symptom of a disease) and/or reduce the risk of developing or worsening a symptom of a disease.

The term "effective amount" or "therapeutically effective amount" of a combination of therapeutic agents is an amount sufficient to provide an observable improvement over the baseline clinically observable signs and symptoms of the disorders treated with the combination.

The term "jointly therapeutically active" or "joint therapeutic effect" as used herein means that the therapeutic agents can be given separately (in a chronologically staggered manner, especially a sequence-specific manner) in such time intervals that they prefer, in the warm-blooded animal, especially human, to be treated, still show a (preferably synergistic) interaction (joint therapeutic effect). Whether this is the case can, inter alia, be determined by following the blood levels, showing that both compounds are present in the blood of the human to be treated at least during certain time intervals.

The term "subject" is intended to include animals. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from cancers.

The terms "comprising" and "including" are used herein in their open-ended and non-limiting sense unless otherwise noted.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

The term "about" or "approximately" usually means within 20%, more preferably within 10%, and most preferably still within 5% of a given value or range. Alternatively, especially in biological systems, the term "about" means within about a log (i.e., an order of magnitude) preferably within a factor of two of a given value.

The pharmaceutical combination of the present invention comprises a MEK inhibitor compound with the following chemical formula (A):

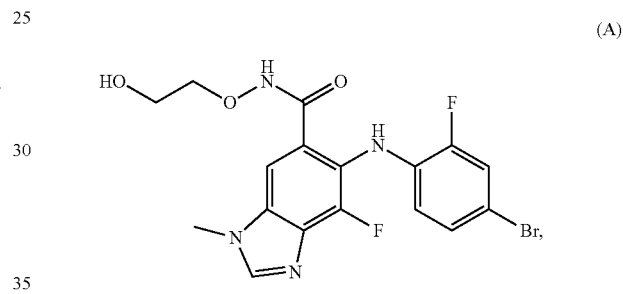

(A)

or pharmaceutically acceptable salts thereof. The compound of formula (A) is also known as the chemical compound 6-(4-bromo-2-fluorophenylamino)-7-fluoro-3-methyl-3H-benzoimidazole-5-carboxylic acid (2-hydroxyethyoxy)-amide (hereinafter referred to as "COMPOUND A"). COMPOUND A is described in PCT Application No. WO 03/077914, which is hereby incorporated by reference in its entirety, and methods for its preparation have been described, for example, in Example 18 therein.

As used herein, the term "pharmaceutically acceptable salts" refers to the nontoxic acid or alkali and alkaline earth metal salts of COMPOUND A. These salts can be prepared in situ during the final isolation and purification of the compound, or by separately reacting the base or acid functions with a suitable organic or inorganic acid or base, respectively.

Acids that can be used to prepare pharmaceutically acceptable acid addition salts of COMPOUND A are those that form non-toxic acid addition salts, i.e., salts containing pharmaceutically acceptable anions, such as the acetate, benzenesulfonate, benzoate, bicarbonate, bisulfate, bitartrate, borate, bromide, calcium, camsylate, carbonate, chloride, clavulanate, citrate, dihydrochloride, edislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palimitate, pantothenate, phosphate/diphosphate, polygalacturonate, salicylate, stearate, subacetate, succinate, tannate, tartrate, teoclate, tosylate, triethiodode, and valerate salts.

With respect to acidic moieties, preferred inorganic salts are those formed with alkali and alkaline earth metals such as lithium, sodium, potassium, barium and calcium. Preferred organic base salts include, for example, ammonium, dibenzylammonium, benzylammonium, 2-hydroxyethylammonium, bis(2-hydroxyethyl)ammonium, phenylethylbenzylamine, dibenzyl-ethylenediamine, and the like salts. Other salts of acidic moieties can include, for example, those salts formed with procaine, quinine and N-methylglusoamine, plus salts formed with basic amino acids such as glycine, ornithine, histidine, phenylglycine, lysine and arginine. An especially preferred salt is a sodium or potassium salt of a compound of the present invention.

With respect to basic moieties, preferred inorganic salts are those formed with an acidic compound, particularly an inorganic acid, such as the hydrochloric, hydrobromic, hydroiodic, sulfuric, phosphoric or the like salts. Preferred organic salts of this type, can include, for example, salts formed with formic, acetic, succinic, citric, lactic, maleic, fumaric, palmitic, cholic, pamoic, mucic, D-glutamic, D-camphoric, glutaric, glycolic, phthalic, tartaric, lauric, stearic, salicyclic, methanesulfonic, benzenesulfonic, paratoluenesulfonic, sorbic, puric, benzoic, cinnamic and the like organic acids. An especially preferred salt of this type is a hydrochloride or sulfate salt.

Unless otherwise specified, or clearly indicated by the text, reference to compounds useful in the combination therapy of the invention includes both the free base of COMPOUND A, and all pharmaceutically acceptable salts of COMPOUND A.

The pharmaceutical combination of the present invention further comprises the IGF1R inhibitory antibody, ANTIBODY A, disclosed in U.S. Pat. No. 7,871,611, which is incorporated herein by reference in its entirety. Specifically, ANTIBODY A comprises the heavy chain amino acid sequence set forth in SEQ ID NO:1 and the light chain amino acid sequence set forth in SEQ ID NO:2, herein.

```
ANTIBODY A heavy chain
                                        (SEQ ID NO: 1)
QVQLQESGPGLVKPSGTLSLTCAVSGGSISSSNWWSWVRQPPGKGLE
WIGEIYHSGSTNYNPSLKSRVTISVDKSKNQFSLKLSSVTAADTAVY
YCARWTGRTDAFDIWGQGTMVTVSSASTKGPSVFPLAPSSKSTSGGT
AALGCLVKDYFPEPVTVSWNSGALTSGVHTFPAVLQSSGLYSLSSVV
TVPSSSLGTQTYICNVNHKPSNTKVDKKVEPKSCDKTHTCPPCPAPE
LLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKA
LPAPIEKTISKAKGQPREPQVYTLPPSRDELTKNQVSLTCLVKGFYP
SDIAVEWESNGQPENNYKTTPPVLDSDGSFFLYSKLTVDKSRWQQGN
VFSCSVMHEALHNHYTQKSLSLSPGK ANTIBODY A light chain
                                        (SEQ ID NO: 2)
DVVMTQSPLSLPVTPGEPASISCRSSQSLLHSNGYNYLDWYLQKPGQ
SPQLLIYLGSNRASGVPDRFSGSGSGTDFTLKISRVEAEDVGVYYCM
QGTHWPLTFGQGTKVEIKRTVAAPSVFIFPPSDEQLKSGTASVVCLL
NNFYPREAKVQWKVDNALQSGNSQESVTEQDSKDSTYSLSSTLTLSK
ADYEKHKVYACEVTHQGLSSPVTKSFNRGEC
```

Variants of ANTIBODY A can also be used in the combination therapy and methods disclosed herein. In one embodiment, the variant is an antibody comprising the heavy chain variable region amino acid sequence set forth in SEQ ID NO:3. In another embodiment, the variant is an antibody comprising the light chain variable region amino acid sequence set forth in SEQ ID NO:4. In another embodiment, the variant is an antibody comprising the heavy chain and light chain variable region amino acid sequences set forth in SEQ ID NO:3 and SEQ ID NO:4, respectively. In yet another embodiment, the variant is an antibody comprising the heavy chain CDR1, 2 and 3 amino acid sequences set forth in SEQ ID NO:5, 6, and 7, respectively. In another embodiment, the variant is an antibody comprising the light chain CDR1, 2 and 3 amino acid sequences set forth in SEQ ID NO:8, 9, and 10, respectively. In a further embodiment, the variant is an antibody comprising the heavy chain CDR1, 2 and 3 amino acid sequences set forth in SEQ ID NO:5, 6, and 7, respectively, and the light chain CDR1, 2 and 3 amino acid sequences set forth in SEQ ID NO:8, 9, and 10, respectively.

Antibody variable region and CDR amino acid sequences of exemplary variants of ANTIBODY A are set forth below:

```
                                        (SEQ ID NO: 3)
QVQLQESGPGLVKPSGTLSLTCAVSGGSISSSNWWSWVRQPPGKGLE
WIGEIYHSGSTNYNPSLKSRVTISVDKSKNQFSLKLSSVTAADTAVY
YCARWTGRTDAFDIWGQGTMVTVSS (SEQ ID NO: 4)
DVVMTQSPLSLPVTPGEPASISCRSSQSLLHSNGYNYLDWYLQKPGQ
SPQLLIYLGSNRASGVPDRFSGSGSGTDFTLKISRVEAEDVGVYYCM
QGTHWPLTFGQGTKVEIK (SEQ ID NO: 5)
SSNWWS (SEQ ID NO: 6)
EIYHSGSTNYNPSLKS (SEQ ID NO: 7)
WTGRTDAFDI (SEQ ID NO: 8)
RSSQSLLHSNGYNYLD (SEQ ID NO: 9)
LGSNRAS (SEQ ID NO: 10)
MQGTHWPLT
```

As used herein, a "combination of agents", "combination of the invention" and similar terms refer to a combination of two types of agents: (1) the MEK inhibitor COMPOUND A or pharmaceutically acceptable salts thereof and (2) the IGF1R inhibitor ANTIBODY A.

Provided herein is a combination therapy comprising a MEK inhibitor (e.g., COMPOUND A) inhibitor and an IGF1R inhibitor (e.g., ANTIBODY A). Administration of the combination of COMPOUND A and ANTIBODY A includes administration of the combination in a single formulation or unit dosage form, administration of the individual agents of the combination concurrently but separately, or administration of the individual agents of the combination sequentially by any suitable route. The dosage of the individual agents of the combination can require more frequent administration of one of the agent(s) as compared to the other agent(s) in the combination. Therefore, to permit appropriate dosing, packaged pharmaceutical products can contain one or more dosage forms that contain the combination of agents, and one or more dosage forms that contain one of the combination of agents, but not the other agent(s) of the combination.

In one embodiment, the present invention comprises a pharmaceutical combination comprising the compound 6-(4-bromo-2-fluorophenylamino)-7-fluoro-3-methyl-3H-benzoimidazole-5-carboxylic acid (2-hydroxyethyoxy)-amide or a pharmaceutically acceptable salt thereof and the IGF1R inhibitor ANTIBODY A for use in the treatment of cancer in a subject in need thereof. The combination of the present invention can be used to treat subjects suffering from, for example, cancers having EGFR amplification, EGFR activating mutations, IGF1R activating signature (e.g., overexpression of IGF1R, high circulating levels of IGF-1, or high levels of IGFBP1), KRAS-mutations, NRAS-mutations and BRAF-mutations.

In a further embodiment, the present invention comprises a pharmaceutical combination comprising the compound 6-(4-bromo-2-fluorophenylamino)-7-fluoro-3-methyl-3H-benzoimidazole-5-carboxylic acid (2-hydroxyethyoxy)-amide or a pharmaceutically acceptable salt thereof and the IGF1R inhibitor ANTIBODY A for use in the treatment of cancers that are resistant or refractive to currently-available therapies, e.g., EGFR amplified, KRAS-mutated cancers, NRAS-mutant and BRAF-mutated cancers that a resistant or refractive to EGFR inhibitors, IGF1-R inhibitors, or BRAF inhibitors, in a subject in need thereof.

In one embodiment, the combination of 6-(4-bromo-2-fluorophenylamino)-7-fluoro-3-methyl-3H-benzoimidazole-5-carboxylic acid (2-hydroxyethyoxy)-amide (COMPOUND A) or a pharmaceutically acceptable salt thereof and ANTIBODY A described herein display a synergistic effect. The term "synergistic effect" as used herein, refers to action of two agents such as, for example, COMPOUND A or a pharmaceutically acceptable salt thereof and ANTIBODY A, producing an effect, for example, slowing the symptomatic progression of cancer or symptoms thereof, which is greater than the simple addition of the effects of each drug administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

Methods of Treatment Using a MEK Inhibitor and an IGF1R Inhibitor Combination

The present invention provides a method of treating cancer in an subject in need thereof by administering a combination of COMPOUND A or a pharmaceutically acceptable salt thereof and ANTIBODY A to the subject in need thereof.

In one embodiment, the present invention provides a method of treating cancer in a subject (e.g., patient) by administering to the subject in need of such treatment a therapeutically effective amount or dose of a combination of COMPOUND A or a pharmaceutically acceptable salt thereof and ANTIBODY A.

In a further embodiment, the present invention provides a method of treating cancer by administering to subject in need of such treatment a quantity of COMPOUND A or pharmaceutically acceptable salt thereof and ANTIBODY A which is jointly therapeutically effective for said treatment.

Examples of types of cancer which can be treated with the combination of the present invention include, without limitation, lung cancer, bone cancer, CMML, pancreatic cancer, skin cancer, cancer of the head and neck, cutaneous or intraocular melanoma, uterine cancer, cancer of the central nervous system (CNS), ovarian cancer, rectal cancer, cancer of the anal region, stomach cancer, colon cancer, breast cancer, melanoma, colorectal cancer, testicular, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis). In certain embodiments, the cancer is a solid tumor.

Further examples of types of cancer which can be treated with the combination of the present invention include, without limitation, adrenocortical carcinoma, AIDS-related cancers, Childhood Cerebellar Astrocytoma, Childhood Cerebral Astrocytoma, Basal Cell Carcinoma, extrahepatic bile duct cancer, osteosarcoma/malignant fibrous histiocytoma bone cancer, brain tumors (e.g., brain stem glioma, cerebellar astrocytoma, cerebral astrocytoma/malignant glioma, ependymoma, medulloblastoma, supratentorial primitive neuroectodermal tumors, visual pathway and hypothalamic glioma), bronchial adenomas/carcinoids, carcinoid tumor, gastrointestinal carcinoid tumor, primary central nervous system, cerebellar astrocytoma, cerebral astrocytoma/malignant glioma, cervical cancer, childhood cancers, Chronic Lymphocytic Leukemia, Chronic Myelogenous Leukemia, Chronic Myeloproliferative Disorders, ependymoma, Ewing's Family of Tumors, extracranial germ cell tumor, extragonadal germ cell tumor, extrahepatic bile duct cancer, intraocular melanoma eye cancer, retinoblastoma eye cancer, gallbladder cancer, gastrointestinal carcinoid tumor, germ cell tumors (e.g., extracranial, extragonadal, and ovarian), gestational trophoblastic tumor, glioma (e.g., adult, childhood brain stem, childhood cerebral astrocytoma, childhood visual pathway and hypothalamic), hairy cell leukemia, hepatocellular cancer, hypopharyngeal cancer, hypothalamic and visual pathway glioma, islet cell carcinoma (endocrine pancreas), Kaposi's Sarcoma, laryngeal cancer, leukemia (e.g., acute lymphoblastic, acute myeloid, chronic lymphocytic, chronic myelogenous, and hairy cell), lip and oral cavity cancer, non-small cell lung cancer, small cell lung cancer, lymphoma (e.g., AIDS-related, Burkitt's, Cutaneous T-Cell, Non-Hodgkin's, and primary central nervous system), Waldenstrom's Macroglobulinemia, malignant fibrous histiocytoma of bone/osteosarcoma, medulloblastoma, merkel cell carcinoma, mesothelioma, metastatic squamous neck cancer with occult primary, multiple endocrine neoplasia syndrome, multiple myeloma/plasma cell neoplasm, mycosis fungoides, myelodysplastic syndromes, myelodysplastic/myeloproliferative diseases, myelogenous leukemia, nasal cavity and paranasal sinus cancer, nasopharyngeal cancer, neuroblastoma, oral cancer, oropharyngeal cancer, ovarian epithelial cancer, ovarian germ cell tumor, ovarian low malignant potential tumor, pancreatic cancer, islet cell pancreatic cancer, parathyroid cancer, pheochromocytoma, pineoblastoma, pituitary tumor, pleuropulmonary blastoma, ureter transitional cell cancer, retinoblastoma, rhabdomyosarcoma, salivary gland cancer, Sezary Syndrome, non-melanoma skin cancer, Merkel Cell Skin Carcinoma, squamous cell carcinoma, testicular cancer, thymoma, gestational trophoblastic tumor, and Wilms' Tumor.

In a preferred embodiment, cancers that can be treated with the combination of the present invention include, without limitation, colorectal cancer, pancreatic cancer, ovarian cancer and melanoma.

The cancer to be treated can have a genetic alteration in the RAS/RAF/MEK signal transduction pathway such as, for example, a HRAS, KRAS, NRAS or BRAF mutation or gene amplification. In one embodiment, the cancer to be treated has a KRAS mutation, e.g., KRAS-mutated colorectal cancer, pancreatic cancer, ovarian cancer and melanoma. In a further embodiment, the cancer to be treated has a BRAF mutation (e.g., BRAF$^{V600}$), e.g, melanoma.

In certain embodiments, the cancer is an EGFR-amplified, KRAS-mutated, NRAS-mutated or a BRAF-mutated cancer. Suitable KRAS-mutated, NRAS-mutated and BRAF-mutated (e.g., BRAF$^{V600}$) cancers include, without limitation, colorectal cancer, pancreatic cancer, ovarian cancer, and melanoma.

In certain embodiments, the cancer is selected from the group consisting of KRAS-mutated colorectal adenocarcinoma, metastatic pancreatic adenocarcinoma, and/or mutant BRAF$^{V600}$ melanoma.

The term "KRAS-mutated cancer" refers to a cancer in which the cancer cells comprise an activating mutation in the RAS family small guanidine triphosphatase (GTPase), KRAS.

The term "NRAS-mutated cancer" refers to a cancer in which the cancer cells comprise an activating mutation in the RAS family kinase small guanidine triphosphatase (GTPase), NRAS. NRAS is also known as neuroblastoma RAS viral (v-ras) homologue.

The term "BRAF-mutated cancer" refers to a cancer in which the cancer cells comprise an activating mutation in the serine/threonine-protein kinase, B-Raf.

The term "BRAF inhibitor" refers to a compound or agent that inhibits, decreases, lowers, or reduces at least one activity of any of the isoforms or mutants of BRAF kinase. Examples of BRAF inhibitors include, but are not limited to, GSK2118436, PLX4720, and PLX4032.

The term "EGFR-amplified cancer" refers to a cancer in which the cancer cells comprise an amplification of the tyrosine kinase domain of epidermal growth factor receptor (EGFR), e.g., EGFR1, EGFR2, or EGFR3.

The term "EGFR inhibitor" refers to a compound that inhibits, decreases, lowers, or reduces at least one activity of an epidermal growth factor receptor (EGFR). Examples of EGFR inhibitors include, but are not limited to, [6,7-bis(2-methoxyethoxy)-4-quinazolin-4-yl]-(3-ethynylphenyl) amine (also known as OSI-774), erlotinib, CI-1033 (formerly known as PD183805), AG-1478, CGP-59326, PKI-166, EKB-569, lapatinib or lapatinib ditosylate; and gefitinib, AG490 (a tyrphostin), ARRY-334543, BIBW-2992, EKB-569, ZD6474, BMS-599626 (Bristol-Myers Squibb), cetuximab, and MDX-447.

The structure of the active agents identified by code nos., generic or trade names can be taken from the actual edition of the standard compendium "The Merck Index" or from databases, e.g., Patents International (e.g., IMS World Publications). The corresponding content thereof is incorporated by reference.

In one embodiment, the present invention provides a method of treating cancer by administering to subject in need of such treatment a quantity of COMPOUND A or pharmaceutically acceptable salt thereof and ANTIBODY A which is jointly therapeutically effective for said treatment.

In a further embodiment, COMPOUND A and ANTIBODY A are in a single formulation or unit dosage form. In a further embodiment, COMPOUND A and ANTIBODY A are in separate formulations or unit dosage forms.

In a further embodiment, COMPOUND A and/or ANTIBODY A are administered at substantially the same time. In a further embodiment, COMPOUND A and/or ANTIBODY A are administered at different times. In a further embodiment, COMPOUND A is administered to the subject prior to administration of ANTIBODY A. In a further embodiment, ANTIBODY A is administered to the subject prior to administration of COMPOUND A.

The present invention further provides a method for treating a cancer that is resistant to refractive to treatment with an EGFR modulator, IGF1R inhibitor, or BRAF inhibitor comprising administering a therapeutically effective amount of COMPOUND A or a pharmaceutically acceptable salt thereof to a subject in need thereof.

In one embodiment, the present invention provides a method for treating a cancer that is resistant or refractive to treatment with the IGF1R inhibitor ANTIBODY A comprising administering a therapeutically effective amount of COMPOUND A or a pharmaceutically acceptable salt thereof to a subject in need thereof.

The present invention further provides a method for the treatment of cancer that is resistant or refractive to treatment with the IGF1R inhibitor ANTIBODY A by administering a therapeutically effective amount of COMPOUND A or a pharmaceutically acceptable salt thereof.

The present invention further provides a use of the pharmaceutical combination comprising COMPOUND A or a pharmaceutically acceptable salt thereof and ANTIBODY A for the manufacture of a pharmaceutical preparation or medicament for the treatment of cancer. In one embodiment, the cancer to be treated is a cancer identified above, which is hereby incorporated by reference in its entirety.

The present invention further provides the use of a pharmaceutical combination comprising COMPOUND A or a pharmaceutically acceptable salt thereof and ANTIBODY A for the manufacture of a pharmaceutical preparation or medicament for the treatment of cancer that is resistant or refractive to treatment with an EGFR modulator, IGF1R inhibitor, or BRAF inhibitor. In one embodiment, the cancer to be treated is a cancer identified above, which is hereby incorporated by reference in its entirety.

The present invention further provides the use of COMPOUND A for the treatment of cancer that is resistant or refractive to treatment with the IGF1R inhibitor ANTIBODY A.

The present invention comprises a pharmaceutical combination comprising COMPOUND A or a pharmaceutically acceptable salt thereof and the IGF1R inhibitor ANTIBODY A for use in the treatment of cancers that are resistant or refractive to currently-available therapies, e.g., EGFR amplified, KRAS-mutated cancers, NRAS-mutant and BRAF-mutated cancers that a resistant or refractive to EGFR inhibitors, IGF1R inhibitors, or BRAF inhibitors, in a subject in need thereof.

Dosages

The optimal dose of the combination of agents for treatment of disease can be determined empirically for each individual using known methods and will depend upon a variety of factors, including, though not limited to, the degree of advancement of the disease; the age, body weight, general health, gender and diet of the individual; the time and route of administration; and other medications the individual is taking. Optimal dosages can be established using routine testing and procedures that are well known in the art.

The amount of combination of agents that can be combined with the carrier materials to produce a single dosage form will vary depending upon the individual treated and the particular mode of administration. In some embodiments the unit dosage forms containing the combination of agents as described herein will contain the amounts of each agent of the combination that are typically administered when the agents are administered alone.

Frequency of dosage can vary depending on the compound used and the particular condition to be treated or prevented. In general, the use of the minimum dosage that is sufficient to provide effective therapy is preferred. Patients can generally be monitored for therapeutic effectiveness using assays suitable for the condition being treated or prevented, which will be familiar to those of ordinary skill in the art.

The dosage form can be prepared by various conventional mixing, comminution and fabrication techniques readily apparent to those skilled in the chemistry of drug formulations.

The oral dosage form containing the combination of agents or individual agents of the combination of agents can be in the form of micro-tablets enclosed inside a capsule, e.g. a gelatin capsule. For this, a gelatin capsule as is employed in pharmaceutical formulations can be used, such as the hard gelatin capsule known as CAPSUGEL, available from Pfizer.

Many of the oral dosage forms useful herein contain the combination of agents or individual agents of the combination of agents in the form of particles. Such particles can be compressed into a tablet, present in a core element of a coated dosage form, such as a taste-masked dosage form, a press coated dosage form, or an enteric coated dosage form, or can be contained in a capsule, osmotic pump dosage form, or other dosage form.

The drug compounds of the present invention (for example, COMPOUND A or a pharmaceutically acceptable salt thereof and ANTIBODY A) are present in the combinations (fixed or non-fixed), dosage forms, pharmaceutical compositions and pharmaceutical formulations disclosed herein in a ratio in the range of 100:1 to 1:100. For example, the ratio of COMPOUND A:ANTIBODY A can be in the range of 1:100 to 1:1, for example, 1:100, 1:90, 1:80, 1:70, 1:60, 1:50, 1:40, 1:30, 1:20, 1:10, 1:5, 1:2, or 1:1. In another example, the ratio of ANTIBODY A:COMPOUND A can be in the range of 1:100 to 1:1, for example, 1:100, 1:90, 1:80, 1:70, 1:60, 1:50, 1:40, 1:30, 1:20, 1:10, 1:5, 1:2, or 1:1.

The optimum ratios, individual and combined dosages, and concentrations of the drug compounds that yield efficacy without toxicity are based on the kinetics of the active ingredients' availability to target sites, and are determined using methods known to those of skill in the art.

The pharmaceutical compositions or combinations provided herein (i.e., COMPOUND A or a pharmaceutically acceptable salt thereof and ANTIBODY A) can be tested in clinical studies. Suitable clinical studies can be, for example, open label, dose escalation studies in patients with cancer. Such studies prove in particular the synergism of the active ingredients of the combination of the invention. The beneficial effects on cancer can be determined directly through the results of these studies which are known as such to a person skilled in the art. Such studies can be, in particular, suitable to compare the effects of a monotherapy using the active ingredients and a combination of the invention. In one embodiment, the dose of COMPOUND A is escalated until the Maximum Tolerated Dosage is reached, and ANTIBODY A is administered with a fixed dose. Alternatively, COMPOUND A can be administered in a fixed dose and the dose of ANTIBODY A can be escalated. Each patient can receive doses of the compounds either daily or intermittently. The efficacy of the treatment can be determined in such studies, e.g., after 12, 18 or 24 weeks by evaluation of symptom scores every 6 weeks.

The administration of a combination therapy of the invention can result not only in a beneficial effect, e.g. a synergistic therapeutic effect, e.g. with regard to alleviating, delaying progression of or inhibiting the symptoms, but also in further surprising beneficial effects, e.g. fewer side-effects, an improved quality of life or a decreased morbidity, compared with a monotherapy applying only one of the pharmaceutically active ingredients used in the combination of the invention.

A further benefit can be that lower doses of the active ingredients of the combination of the invention can be used, for example, that the dosages need not only often be smaller but can also be applied less frequently, which can diminish the incidence or severity of side-effects. This is in accordance with the desires and requirements of the patients to be treated.

It is one objective of this invention to provide a pharmaceutical combination comprising a quantity, which can be jointly therapeutically effective at targeting or preventing cancer, e.g., a EGFR amplified, KRAS-mutated, NRAS-mutated or BRAF-mutated cancer. In this combination, COMPOUND A and ANTIBODY A can be administered together, one after the other or separately in one combined unit dosage form or in two separate unit dosage forms. The unit dosage form can also be a fixed combination.

The pharmaceutical compositions for separate administration (or non-fixed dose) of both compounds, or for the administration in a fixed combination, i.e. a single composition comprising both compounds according to the invention can be prepared in a manner known per se and are those suitable for enteral, such as oral or rectal, and parenteral administration to mammals (warm-blooded animals), including humans, comprising a therapeutically effective amount of at least one pharmacologically active combination partner alone, e.g. as indicated above, or in combination with one or more pharmaceutically acceptable carriers or diluents, especially suitable for enteral or parenteral application.

In one embodiment, the present invention relates to a pharmaceutical composition or pharmaceutical formulation comprising (a) COMPOUND A or a pharmaceutically acceptable salt thereof, and (b) ANTIBODY A, and optionally one or more pharmaceutically acceptable carriers.

In a further embodiment, the present invention further relates to a pharmaceutical composition or pharmaceutical formulation comprising (a) COMPOUND A or a pharmaceutically acceptable salt thereof, and (b) ANTIBODY A, and optionally one or more pharmaceutically acceptable carriers, for use in the treatment of cancer.

In a further embodiment, the present invention relates to (a) a pharmaceutical combination comprising COMPOUND A or a pharmaceutically acceptable salt thereof, and (b) a pharmaceutical composition comprising ANTIBODY A administered in separate pharmaceutical compositions to a subject in need thereof.

Formulations

The drug combinations provided herein can be formulated by a variety of methods apparent to those of skill in the art of pharmaceutical formulation. As discussed above, COMPOUND A and ANTIBODY A can be formulated into the same pharmaceutical composition or into separate pharmaceutical compositions for individual administration. Suitable formulations include, for example, tablets, capsules, press coat formulations, intravenous solutions or suspensions, and other easily administered formulations.

One or both combination partners can be administered in a pharmaceutical formulation comprising one or more pharmaceutically acceptable carriers. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

Suitable pharmaceutical formulations can contain, for example, from about 0.1% to about 99.9%, preferably from about 1% to about 60%, of the active ingredient(s). Pharmaceutical formulations for the combination therapy for enteral or parenteral administration are, for example, those in unit dosage forms, such as sugar-coated tablets, tablets, capsules or suppositories, or ampoules. If not indicated otherwise, these are prepared in a manner known per se, for example by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units.

In accordance with the present invention, a therapeutically effective amount of each of the combination partners of the combination of the invention can be administered simultaneously or sequentially and in any order, and the components can be administered separately or as a fixed combination. Alternatively, an amount, which is jointly therapeutically effective for the treatment of cancer, of each combination partner of the combination of the invention can be administered simultaneously or sequentially and in any order, and the components can be administered separately or as a fixed combination.

For example, the method of treating a disease according to the invention can comprise (i) administration of the first agent in free or pharmaceutically acceptable salt form and (ii) administration of the second agent in free or pharmaceutically acceptable salt form, simultaneously or sequentially in any order, in jointly therapeutically effective amounts, preferably in synergistically effective amounts, e.g. in daily or intermittently dosages corresponding to the amounts described herein. The individual combination partners of the combination of the invention can be administered separately at different times during the course of therapy or concurrently in divided or single combination forms. Furthermore, the term administering also encompasses the use of a pro-drug of a combination partner that convert in vivo to the combination partner as such. The instant invention is therefore to be understood as embracing all such regimens of simultaneous or alternating treatment and the term "administering" is to be interpreted accordingly.

The effective dosage of each of the combination partners employed in the combination of the invention can vary depending on the particular compound or pharmaceutical composition employed, the mode of administration, the condition being treated, the severity of the condition being treated. Thus, the dosage regimen of the combination of the invention is selected in accordance with a variety of factors including the route of administration and the renal and hepatic function of the patient. A clinician or physician of ordinary skill can readily determine and prescribe the effective amount of the single active ingredients required to alleviate, counter or arrest the progress of the condition. A clinician or physician of ordinary skill can also readily determine the effective dosage using the Response Evaluation Criteria In Solid Tumors (RECIST) guidelines (see e.g., Therasse et al. 2000, JNCI 92:2, 205, which is hereby incorporated by reference in its entirety).

Suitable dosages for COMPOUND A used in the methods described herein are on the order of about 0.1 mg to about 200 mg, (e.g., about 0.1, 0.3, 0.5, 0.7, 1, 3, 5, 10, 15, 20, 25, 30, 35, 40, 45, 50, 55, 60, 65, 70, 75, 80, 90, 95, 100, 120, 140, 160, 180, 200, or 220 mg). In a preferred embodiment, COMPOUND A is administered to a subject at a dosage of about 15 mg, 30 mg, 45 mg, or 60 mg.

Suitable dosages for ANTIBODY A used in the methods described herein are on the order of about 1 mg/kg to about 100 mg/kg, (e.g., about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 90, 95, or 100 mg/kg). In a preferred embodiment, ANTIBODY A is administered to a subject at a dosage of about 9, 12 or 20 mg/kg.

Suitable administration frequencies for COMPOUND A or ANTIBODY A used in the methods described herein are on the order of about 10 times per day to about once per month (e.g., about 10, 9, 8, 7, 6, 5, 4, 3, 2, 1 times per day to about 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 times per month).

In one embodiment, between about 15 and about 60 mg of COMPOUND A is administered orally twice daily to a subject. In another embodiment, ANTIBODY A is administered intravenously twice per month at between about 9 and about 20 mg/kg.

The invention is further illustrated by the following examples. The examples should not be construed as further limiting. The beneficial effects of the combination of the invention can also be determined by other test models known to the person skilled in the pertinent art.

EXAMPLE 1

Synthesis of COMPOUND A

The synthesis of COMPOUND A is described in International Patent Application WO 03/077914 (PCT/US03/07864), which is incorporated by reference in its entirety. The synthesis of this compound is described below.

2,3,4-Trifluoro-5-nitro-benzoic acid 2

A 3 liter three neck round bottom flask is charged with 125 ml $H_2SO_4$. Fuming nitric acid is added (8.4 ml, 199 mmol) and the mixture gently stirred. 2,3,4-Trifluorobenzoic acid 1 (25 g, 142 mmol) is added in 5 g portions over 90 minutes. The dark brownish yellow solution is stirred for 60 min at which time the reaction is complete. The reaction mixture is poured into 1 liter of an ice:water mixture and extracted with diethyl ether (3×600 ml). The combined organic extracts are dried ($MgSO_4$) and concentrated under reduced pressure to give a yellow solid. The solid is suspended in hexanes and stirred for 30 min after which time it is filtered to give 29 g (92%) of clean desired product as an off-yellow solid: MS APCI (−) m/z 220 (M-1) detected.

4-Amino-2,3-difluoro-5-nitro-benzoic acid 3

Ammonium hydroxide solution (~30% in water) (35 ml, 271 mmol) is added to a solution of 2,3,4-trifluoro-5-nitro-benzoic acid 2 (15 g, 67.8 mmol) in 30 ml water at 0° C. with stirring. Upon completion of ammonium hydroxide addition the reaction mixture is warmed to room temperature with stirring. After 2.5 h, the reaction mixture is cooled to 0° C. and concentrated HCl is carefully added until pH of reaction mixture is near 0. The reaction mixture is diluted with water (30 ml) and extracted with diethyl ether (3×50 ml). The combined organic extracts are dried (MgSO$_4$) and concentrated under reduced pressure to give 14 g (95%) of pure desired product: MS APCI (−) m/z 217 (M-1) detected.

4-Amino-2,3-difluoro-5-nitro-benzoic acid methyl ester 4

A 2 M solution of TMS diazomethane in hexanes (6.88 ml, 13.75 mmol) is added to a suspension of 4-amino-2,3-difluoro-5-nitro-benzoic acid 3 (2.00 g, 9.17 mmol) in 25 ml of 4:1 THF:MeOH at 0° C. under nitrogen atmosphere. Upon completion of addition, reaction mixture is warmed to room temperature. After 0.5 h, excess TMS diazomethane is destroyed by the careful addition of acetic acid. The reaction is then concentrated under reduced pressure and dried in vacuo to give 1.95 g (92%) of pure desired product: MS APCI (−) m/z 231 (M-1) detected.

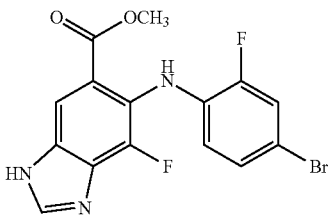 [SMILES: COC(=O)c1cc2[nH]cnc2c(F)c1Nc1ccc(Br)cc1F]

6-(4-Bromo-2-fluoro-phenylamino)-7-fluoro-3H-benzoimidazole-5-carboxylic acid methyl ester (8d)

Step A: 4-Amino-3-fluoro-2-(2-fluoro-phenylamino)-5-nitro-benzoic acid methyl ester 5b 4-Amino-2,3-difluoro-5-nitro-benzoic acid methyl ester 4 (1.50 g, 6.46 mmol) is suspended in xylenes (7.5 mL) and 2-fluoro-phenylamine (6.24 mL, 64.6 mmol) is added. The reaction mixture is stirred at 140° C. under N$_2$. After stirring for 6 days, the reaction is complete. The reaction mixture is cooled to room temperature and diluted with methylene chloride and filtered through a silica gel plug eluting with methylene chloride (1 L) to give an orange filtrate. The filtrate is concentrated to dryness and then triturated with diethyl ether to yield a bright yellow solid. The trituration is repeated. The yellow solid is collected to yield 1.08 g (52%) of the pure desired product. MS APCI (−) m/z 322 (M-1) detected.

Step B: 6-(4-Bromo-2-fluoro-phenylamino)-7-fluoro-3H-benzoimidazole-5-carboxylic acid methyl ester 8d 4-Amino-3-fluoro-2-(2-fluoro-phenylamino)-5-nitro-benzoic acid methyl ester 5b is converted by reduction/cyclization and bromination procedures to yield the desired product. MS ESI (+) m/z 382, 384 (M+, Br pattern) detected.

6-(4-bromo-2-fluorophenylamino)-7-fluoro-3-methyl-3H-benzoimidazole-5-carboxylic acid (2-hydroxyethoxy)-amide A solution of 6-(4-Bromo-2-fluoro-phenylamino)-7-fluoro-3H-benzoimidazole-5-carboxylic acid methyl ester (8d), iodomethane and potassium carbonate in dimethylformamide is stirred at 75° C. for one hour. The reaction mixture is diluted with ethyl acetate, washed with saturated aqueous potassium carbonate (2×), brine, and dried (Na$_2$SO$_4$). Flash column chromatography (20:1 methylene chloride/ethyl acetate) provides the 3-methyl-3H-benzoimidazole compound.

The 3-methyl-3H-benzoimidazole compound is dissolved into 2:1 THF/water and NaOH (1.0 M aqueous solution) is added. After stirring for two hours the reaction is reduced to one quarter initial volume via rotary evaporation and the remainder diluted with water. The aqueous solution is acidified to pH 2 by the addition of 1.0 M aqueous HCl and extracted with 1:1 tetrahydrofuran/ethyl acetate (3×), dried (Na$_2$SO$_4$) and concentrated under reduced pressure to provide pure carboxylic acid as an off white solid. The carboxylic acid, O-(2-vinyloxy-ethyl)-hydroxylamine, HOBt, triethylamine and EDCI are dissolved in dimethylformamide and stirred at room temperature for 48 hours. The reaction mixture is diluted with ethyl acetate, washed with water (3×), saturated potassium carbonate (2×), saturated ammonium chloride (2×), brine, dried (Na$_2$SO$_4$) and concentrated under reduced pressure to an off-white solid of 6-(4-bromo-2-fluoro-phenylamino)-7-fluoro-3-methyl-3H-benzoimidazole-5-carboxylic acid (2-vinyloxy-ethoxy)-amide.

Hydrochloric acid (14 mL, 1.0 M aqueous solution, 14 mmol) is added to a suspension of the previous compound in ethanol and the reaction mixture allowed to stir for 24 hours. The reaction mixture is concentrated to dryness by rotary evaporation and the solids partitioned between 3:1 ethyl acetate/tetrahydrofuran and saturated potassium carbonate. The aqueous phase is extracted with 3:1 ethyl acetate/tetrahydrofuran (3×), the combined organics dried (Na$_2$SO$_4$), and concentrated to 6-(4-bromo-2-fluoro-phenylamino)-7-fluoro-3-methyl-3H-benzoimidazole-5-carboxylic acid (2-hydroxy-ethoxy)-amide as an off-white solid.

EXAMPLE 2

Phase Ib/II Open-Label, Multi-Center Study of the Combination of MEK Inhibitor COMPOUND a and Insulin-Like Growth Factor-1 Receptor (IGF1R) Inhibitor ANTIBODY A in Adult Patients with Selected Advanced Solid Tumors A multi-center, open-label, phase Ib/II study is conducted evaluating the efficacy and safety of the combination of the MEK inhibitor of COMPOUND A and the Insulin-like growth factor-1 receptor (IGF1R) inhibitor of ANTIBODY A in adult patients with selected advanced solid tumors. First, a dose-escalation Phase Ib study is conducted to estimate the maximal terminal dose(s) (MTDs) and/or to identify the recommended Phase II dose(s) (RP2D) for the combination of MEK inhibitor COMPOUND A and Insulin-like growth factor-1 receptor (IGF1R) inhibitor ANTIBODY A in patients. Second, a Phase II is conducted to assess the clinical efficacy and to further assess the safety of this combination in select patients.

Dose-Escalation Study

Patients with documented advanced KRAS- or BRAF-mutant cancers, such as colorectal cancer (CRC), pancreatic cancer and melanoma or other advanced solid tumors, or pancreatic cancer (regardless of KRAS- or BRAFV600 mutational status) are enrolled. Each enrolled patient is determined to satisfy the specific inclusion/exclusion criteria set forth below. For this dose-escalation study, approximately 15-25 patients are enrolled.

In this study, COMPOUND A is administered as an oral tablet twice-daily (BID) in 28-day cycles. ANTIBODY A is administered as a solution for intravenous infusion every second week (Q2W) on days 1 and 15 of every cycle.

All patients are administered a starting dose for the combination of 30 mg BID COMPOUND A and 12 mg/kg Q2W ANTIBODY A. The dose is continuously escalated until MTD(s)/RP2D9s) is/are reached. Patients are dosed on a flat scale with COMPOUND A, and patients are dosed with ANTIBODY A according to body weight. During escalation, only one study drug is escalated a time as follows:

| Dose Level | COMPOUND A mg BID | COMPOUND B mg/kg Q2W |
|---|---|---|
| −1b* | 15 | 12 |
| −1a* | 30 | 9 |
| Starting Dose level 1 | 30 | 12 |
| 2 | 45 | 12 |
| 3 | 45 | 20 |
| 4 | 60 | 20 |

*"a"- and "b"-dose levels can be explored in parallel.

The dose escalation part of the study is guided by a Bayesian Logistic Regression Model (BLRM). At all decision time points, the adaptive BLRM permits alterations in the dose increments based on the observed dose-limiting toxicities (DLTs). No dosages below 15 mg BID COMPOUND A or 9 mg/kg Q2W of ANTIBODY A are permitted.

DLTs are assessed using the National Cancer Institute (NCI) Common Toxicity Criteria for Adverse Events (CTCAE), version 4.03. Parameters monitored on the patients are, for example, clinical examination, blood and lymphatic system disorders, cardiac disorders, vascular disorders, general disorders and administration site conditions, skin and subcutaneous tissue disorders (e.g., rash or photosensitivity), hyperglycemia, gastrointestinal disorders, blood bilirubin, AST or ALT levels, serum alkaline phosphatase, serum lipase and/or serum amylase (asymptomatic) serum creatine, serum CK/CPK, ANC, platelet count, ECG QTc interval, eye disorders (e.g., retinopathy, blurred vision, flashing lights, floaters), hearing impairment, and other hematologic and non-hematologic toxicities.

The MTD is defined as the highest combination drug dosage not causing medically unacceptable DLT in more than 35% of the treated patients in the first cycle of treatment. Since several combinations can correspond to this definition more than one MTD can be identified with different doses of the study drugs. The applied adaptive Bayesian methodology provides an estimate of the combinations of COMPOUND A and ANTIBODY A not exceeding the MTD. Typically the MTD is a tested dose with maximum probability of targeted toxicity (DLT rate between 16%-35%). The use of EWOC principle limits the risk that a potential next dose will exceed the MTD (Section 10.4.2).

Patients are discontinued from the study if: (a) a dose delay of >21 consecutive days of COMPOUND A and/or more than 2 consecutive doses of ANTIBODY A from the intended day of the next scheduled dose, or (b) adverse events or an abnormal laboratory value. Any patients whose treatment is interrupted or permanently discontinued due to an adverse event or clinically significant laboratory issue is followed up at least once a week for 4 weeks. A maximum of two (2) dose reductions are allowed and, upon dose reduction, no dose re-escalation is permitted.

Inclusion and Exclusion Criteria:
The inclusion criteria for the patients are the following:
Age≥18 years
Male or female patients with either (a) advanced solid tumors (including but not limited to colorectal cancer (CRC), pancreatic cancer and melanoma and other advanced solid tumors) with documented somatic KRAS- or BRAFV600 mutations in tumor tissue, or (b) metastatic pancreatic adenocarcinoma irrespective of KRAS or BRAFV600 mutational status. In Phase II, this criteria is modified as follows: (a) For Arm 1 only—Patients with KRAS-mutant colorectal adenocarcinoma, (b) For Arm 2 only—Patients with metastatic pancreatic adenocarcinoma (adenocarcinoma irrespective of KRAS or BRAFV600 mutational status, and (c) For Arm 3 only—Patients with mutant BRAFV600 melanoma.

Patient relapsed or progressed following standard therapy or patients for whom no standard anticancer therapy according to investigator assessment exists.

Measurable disease as determined by RECIST v1.1. World Health Organization (WHO) Performance Status (PS) ≤2. Target legions in previously irradiated areas should not be selected unless there is clear evidence of progression in such lesions.

Adequate organ function and laboratory parameters as defined by: absolute neutrophil count (ANC)≥1.5×109/L; Hemoglobin (Hgb)≥9 g/dl; Platelets (PLT)≥100×109/L without transfusions within 21 days before first treatment; AST/SGOT and/or ALT/SGPT≤2.5×ULN (upper limit of normal) or ≤5×ULN if liver metastases are present; Serum bilirubin≤2×ULN; Serum creatinine≤1.5×ULN or calculated or directly measured CrCl≥50% LLN (lower limit of normal); Negative serum pregnancy test.

Recovery from all AEs of previous anti-cancer therapies, including surgery and radiotherapy, to baseline or to CTCAE Grade ≤1, except for alopecia.

Negative serum pregnancy (β hCG) test within 72 hrs before starting study treatment in all pre-menopausal women and women <12 months after the onset of menopause.

The exclusion criteria for the patients are the following:
Prior therapy with any MEK inhibitor or IGF1R inhibitor.
History or current evidence of central serous retinopathy (CSR), retinal vein occlusion (RVO) or retinal degenerative disease
Patients with known history of severe infusion reactions to monoclonal antibodies
Patients with primary CNS tumor or CNS tumor involvement, unless patient suffers from metastatic CNS tumor and the following additional criteria are satisfied: (a) 4 weeks from prior therapy completion (including radiation and/or surgery), (b) clinically stable with respect to the CNS tumor at the time of study entry, (c) not receiving steroid therapy, and (d) not receiving anti-convulsive medications (that were started for brain metastases).
Patients who have received prior systemic anti-cancer treatment within the following time frames: (a) Cyclical chemotherapy within a period of time that is shorter than the cycle length used for that treatment (e.g. 6 weeks for nitrosourea, mitomycin-C) prior to starting study treatment, and (b) Biologic therapy (e.g. antibodies), continuous or intermittent small molecule therapeutics, or any other investigational agents within a period of time which is ≤5 T½ or ≤4 weeks (whichever is shorter) prior to starting study treatment.
Patients who have received radiotherapy ≤4 weeks prior to starting study drug, who have not recovered from side effects of such therapy and/or from whom ≥30% of the bone marrow was irradiated.

Patients who have undergone major surgery ≤4 weeks prior to starting study treatment or who have not recovered from side effects of such procedure.

History of thromboembolic event requiring full-dose anti-coagulation therapy any time prior to enrollment Clinically significant cardiac disease or impaired cardiac function. Patients with diabetes mellitus requiring insulin treatment and/or with clinical signs or with fasting plasma glucose >160 mg/dL (8.9 mmol/L).

Patients with peripheral neuropathy CTCAE Grade ≥2.

Patients with diarrhea CTCAE Grade ≥2.

Patients with acute or chronic pancreatitis.

Patients with external biliary drains.

Any other condition that would, in the Investigator's judgment, contraindicate patient's participation in the clinical study due to safety concerns or compliance with clinical study procedures, e.g. infection/inflammation, intestinal obstruction, unable to take oral medication, social/psychological complications.

Impaired GI function or GI disease that can significantly alter the absorption of oral COMPOUND A (e.g. ulcerative disease, uncontrolled nausea, vomiting, diarrhea, malabsorption syndrome, or small bowel resection).

Patients treated with hematopoietic colony-stimulating growth factors (e.g. G-CSF, GM-CSF, M-CSF) ≤2 weeks prior to starting study drug. Erythropoietin or darbepoetin is allowed as long as it has been initiated at least 2 week prior to study enrollment.

Patients who have received systemic corticosteroids ≤2 weeks prior to starting study drug, or who have not fully recovered from side effects of such treatment.

History of another malignancy within 2 years, except cured basal cell carcinoma of the skin or excised carcinoma in situ of the cervix.

Known positive serology for HIV, active Hepatitis B, and/or active Hepatitis C infection.

Pregnant or nursing (lactating) women, where pregnancy is defined as the state of a female after conception and until the termination of gestation, confirmed by a positive hCG laboratory test (>5 mIU/mL).

Women of child-bearing potential, defined as all women physiologically capable of becoming pregnant, are not allowed to participate in this study UNLESS they are using highly effective methods of contraception throughout the study and for 30 days after study drug discontinuation.

Efficacy Study

Following MTD/RP2D declaration, patients are enrolled in three Phase II arms to assess efficacy of the combination: (a) Arm 1 consists of patients with KRAS-mutant colorectal adenocarcinoma, (b) Arm 2 consists of patients with metastatic pancreatic adenocarcinoma, and (c) Arm 3 consist of patients with mutant BRAF$^{V600}$ melanoma. Approximately 20-30 patients are enrolled in each of Arms 1, 2 and 3.

Patients are administered a suitable dosage of the combination of COMPOUND A and ANTIBODY A as defined in the dose-escalation Phase Ib study.

Efficacy of the administered combination of COMPOUND A and ANTIBODY A is assessed by comparison of the tumor progression from baseline/screening. All potential sites of tumor lesions are assessed at baseline/screening by radiologic techniques (e.g., CT or MRI imaging) or physical examination (e.g. subcutaneous nodules and measurable cutaneous lesions). The methods of measurement are following the RECIST version 1.1 criteria for solid tumors. While enrolled in the study, follow-up tumor assessments are performed after completion of 6 weeks of treatment (Cycle 2, Day 15), 10 weeks of treatment (Cycle 3, Day 15), 16 weeks of treatment (Cycle 5, Day 1), 22 weeks of treatment (Cycle 6, Day 15), 28 weeks of treatment (Cycle 14, Day 1) and every 12 weeks thereafter (start of the every 3$^{rd}$ cycle) and at the end of treatment visit.

Patients are treated until progression of disease, unacceptable toxicity develops, or withdrawal of informed consent, whichever occurs first. All patients are followed up—at minimum, patients must complete the safety follow-up assessments 30 days after the last dose of the study treatment. Patients do not progress at the time of discontinuation of study treatment are radiologically followed for the disease status and phase II patients are followed for survival. The study is ending upon completion of the follow-up period of the last patient treated with the combination. However, the safety and efficacy of the combination is assessed with clinical trial data obtained prior to study end.

EXAMPLE 3

Effect of the Combination of COMPOUND A and ANTIBODY A on the Proliferation of KRAS Mutant Pancreatic Cancer Cell Lines A cell proliferation assay was performed to investigate the activity of the combination of COMPOUND A and ANTIBODY A on Insulin-like Growth Factor 1 (IGF1)-induced proliferation of the KRAS mutant cell lines Miapaca-2 and AsPC-1. To evaluate the combination effect in a non-biased way, and to identify synergistic effects at different concentrations, the study was conducted using a "dose matrix" scheme (described in detail below). The results of these experiments, set forth below, demonstrated that the combination of COMPOUND A and ANTIBODY A synergistically inhibited IGF1-induced proliferation of Miapaca-2 and AsPC-1 in the absence of IGF1, when compared to each agent acting alone.

Preparation of Compound Solutions

COMPOUND A (10 mM) was stored in aliquots at −20° C. ANTIBODY A (0.2 mM in 1% BSA) was stored in aliquots at 4° C. Insulin-like Growth Factor-1 (IGF1; R&D System, Cat #291-G1) was reconstituted at 100 ug/mL in sterile Phosphate Buffered Saline (PBS).

Cell Culture

The KRAS mutant, pancreatic cancer cell lines Miapaca-2 and AsPC-1 were cultured in DMEM medium (ATCC Cat #30-2002) and RPMI-1640 (ATCC Cat #30-2001) plus 10% Fetal Bovine Serum (FBS; Invitrogen Cat #10099-141) as recommended by the supplier. Cells were cultured in T-150 flasks using standard cell culture techniques and split upon reaching 80% confluency. TryPLE Express (Invitrogen #12604-013, no phenal red) was used for all cell dissociation. Cell count and viability were measured using Trypan dye exclusion with a ViCell counter (Beckman-Coulture). Cells were determined to be free of Mycoplasma using a PCR detection method (www.radil.missouri.edu).

Cell Viability Assay and Cell Proliferation Assay

Miapaca-2 and AsPC-1 cells were trypsinized using TryPLE Express and plated (1200 cells/well) on clear-bottom 384-well black plates (Greiner) in triplicate (30 μL/well in culture media). Cells were allowed to attach overnight followed by 120 hours of incubation with various concentrations of inhibitor agents or agent combinations (10 μL/well) in the presence or absence of IGF1. Cell viability was determined by measuring cellular ATP content using the CellTiter-Glo® (CTG) luminescent cell viability assay (Promega). Each single agent and combination treatment was compared to control, or cells treated with an equivalent volume of medium.

An equal volume of the CTG reagents was added to each well at the end of the compound treatment and luminescence was recorded on an Envision plate reader (Perkin Elmer). Reduced and enhanced luminescent signal values (responses) were calculated relative to untreated (control) cells.

Method for Calculating the Efficacy of Combinations of COMPOUND A and ANTIBODY A To evaluate the anti-proliferative activity of COMPOUND A with ANTIBODY A in a non-biased way, as well as to identify synergistic effects at various concentrations, the studies were conducted using a "dose matrix." This dose matrix utilized different permutations of serially-diluted single agents (e.g., COMPOUND A and ANTIBODY A). In combination assays, agents were applied simultaneously and were assessed in the presence and absence of IGF1. COMPOUND A was subjected to a 7 dose 3× serial dilution, with a high dose of 2.6 µM and a low dose of approximately 3.5 nM. ANTIBODY A was subjected to a 6 dose 3× serial dilution with a high dose of 566 nM and a low dose of approximately 2.3 nM.

The synergistic interaction of COMPOUND A with ANTIBODY A (analyzed using Chalice software [CombinatoRx, Cambridge Mass.]) was calculated by comparing the response from a combination to the response of the agent acting alone, against the drug-with-itself dose-additive reference model. Deviations from dose additives was assessed numerically with a Combination Index (CI), which quantifies the overall strength of combination effect. This calculation (essentially a volume score) is as follows: $V_{HSA} = \Sigma_{X,Y} \ln f_X \ln f_Y (I_{data} - I_{HSA})$. CI was calculated between the data and the highest single-agent surface, normalized for single agent dilution factors (see e.g., Lehar J et al (2009), "Synergistic drug combinations tend to improve therapeutically relevant selectivity", Nature Biotechnology 27: 659-66 (2009)).

All data evaluation and graph generation were performed using Microsoft Excel software, and Chalice software.

Results

The percentage inhibition of IGF1-induced proliferation of Miapaca-2 and AsPC-1 cells under each condition of the dose matrix is set forth in FIG. 1. COMPOUND A displayed concentration dependent anti-proliferative activity in both the presence and absence of IGF1, and the addition of IGF1 appeared to slightly dampen the single agent activity of COMPOUND A. ANTIBODY A was almost totally inactive in the presence or absence of IGF1. The combination of COMPOUND A and ANTIBODY A exhibited a synergistic affect when applied to Miapaca-2 cells in the absence of IGF1, as evidenced by the difference in the inhibition of cell proliferation exhibited by each agent alone. Enhancement of growth inhibition was observed when 288 nM-2.6 µM COMPOUND A was combined with 189 nM-566 nM ANTIBODY A (see FIG. 1). In contrast, in the presence of IGF1, no synergy or enhanced growth inhibition was observed.

These data demonstrate that the combination of COMPOUND A and ANTIBODY A synergistically inhibits the growth of KRAS mutant pancreatic cancers in the absence of IGF1 signaling. Thus, the combination of COMPOUND A and ANTIBODY A represents an improved treatment for KRAS mutant pancreatic cancers.

---

We claim:

1. A method of treating cancers expressing insulin-like growth factor-1 receptor (IGF1R) in a subject in need thereof, comprising administering to the subject a therapeutically effective amount of
   (a) the compound 6-(4-bromo-2-fluorophenylamino)-7-fluoro-3-methyl-3H-benzoimidazole-5-carboxylic acid (2-hydroxyethyoxy)-amide (COMPOUND A) or a pharmaceutically acceptable salt thereof; and
   (b) an antibody that specifically binds to insulin-like growth factor-1 receptor (IGF1R), wherein the antibody comprises the heavy and light chain amino acid sequences set forth in SEQ ID NO:1 and SEQ ID NO:2, respectively;
   wherein the cancer is resistant or refractory to treatment with a EGFR inhibitor, IGF1R inhibitor or BRAF inhibitor as a monotherapy.

2. The method of claim 1, wherein COMPOUND A or a pharmaceutically acceptable salt thereof and the antibody are in a single formulation or unit dosage form.

3. The method of claim 1, wherein COMPOUND A or a pharmaceutically acceptable salt thereof and the antibody are in separate formulations or unit dosage forms.

4. The method of claim 1, wherein COMPOUND A or a pharmaceutically acceptable salt thereof and/or the antibody are administered at substantially the same time.

5. The method of claim 1, wherein COMPOUND A or a pharmaceutically acceptable salt thereof and/or the antibody are administered at different times.

6. The method of claim 1, wherein the cancer is selected from the group consisting of lung cancer, bone cancer, CMML, pancreatic cancer, skin cancer, cancer of the head and neck, cutaneous or intraocular melanoma, uterine cancer, cancer of the central nervous system (CNS), ovarian cancer, rectal cancer, cancer of the anal region, stomach cancer, colon cancer, breast cancer, melanoma, colorectal cancer, testicular, gynecologic tumors, Hodgkin's disease, cancer of the esophagus, cancer of the small intestine, cancer of the endocrine system, sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter, adrenocortical carcinoma, AIDS-related cancers, Childhood Cerebellar Astrocytoma, Childhood Cerebral Astrocytoma, Basal Cell Carcinoma, extrahepatic bile duct cancer, osteosarcoma/malignant fibrous histiocytoma bone cancer, brain tumors, bronchial adenomas/carcinoids, carcinoid tumor, gastrointestinal carcinoid tumor, primary central nervous system, cerebellar astrocytoma, cerebral astrocytoma/malignant glioma, cervical cancer, childhood cancers, Chronic Lymphocytic Leukemia, Chronic Myelogenous Leukemia, Chronic Myeloproliferative Disorders, ependymoma, Family of Tumors, extracranial germ cell tumor, extragonadal germ cell tumor, extrahepatic bile duct cancer, intraocular melanoma eye cancer, retinoblastoma eye cancer, gallbladder cancer, gastrointestinal carcinoid tumor, germ cell tumors, gestational trophoblastic tumor, glioma, hairy cell leukemia, hepatocellular cancer, hypopharyngeal cancer, hypothalamic and visual pathway glioma, islet cell carcinoma, Kaposi's Sarcoma, laryngeal cancer, leukemia, lip and oral cavity cancer, non-small cell lung cancer, small cell lung cancer, lymphoma, Waldenstrom's Macro lobulinemia malignant fibrous histiocytoma of bone/osteosarcoma, medulloblastoma, merkel cell carcinoma, mesothelioma, metastatic squamous neck cancer with occult primary, multiple endocrine neoplasia syndrome, multiple myeloma/plasma cell neoplasm, mycosis fungoides, myelodysplastic syndromes, myelodysplastic/myeloproliferative diseases, myelogenous leukemia, nasal cavity and paranasal sinus cancer, nasopharyngeal cancer, neuroblastoma, oral cancer, oropharyngeal cancer, ovarian epithelial cancer, ovarian germ cell tumor, ovarian low malignant potential tumor, pancreatic cancer, islet cell pancreatic cancer, parathyroid cancer, pheochromocytoma, pineoblastoma, pituitary tumor, pleuropulmonary blastoma, ureter transitional cell cancer, retinoblastoma, rhabdomyosarcoma, salivary gland cancer, Sezary Syndrome, non-melanoma skin cancer, Merkel Cell Skin Carcinoma, squamous cell carcinoma, testicular cancer, thymoma, gestational trophoblastic tumor, and Wilms' Tumor.

7. The method of claim 1, wherein COMPOUND A is administered at a dosage of between about 15 and 60 mg.

8. The method of claim 1, wherein COMPOUND A is administered at a dosage of between 15 and 60 mg.

9. The method of claim 1, wherein the antibody is administered at a dosage of between about 9 and 20 mg/kg.

10. The method of claim 1, wherein the antibody is administered at a dosage of between 9 and 20 mg/kg.

* * * * *

SEQUENCE LISTING

```
<160> NUMBER OF SEQ ID NOS: 10

<210> SEQ ID NO 1
<211> LENGTH: 449
<212> TYPE: PRT
<213> ORGANISM: Artificial Sequence
<220> FEATURE:
<223> OTHER INFORMATION: Synthetic: antibody A heavy chain

<400> SEQUENCE: 1

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Trp Thr Gly Arg Thr Asp Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 2
<211> LENGTH: 219
<212> TYPE: PRT
<213> ORGANISM: Artificial Sequence
<220> FEATURE:
<223> OTHER INFORMATION: Synthetic: antibody A light chain

<400> SEQUENCE: 2

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
            85                  90                  95

Thr His Trp Pro Leu Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 3
<211> LENGTH: 119
<212> TYPE: PRT
<213> ORGANISM: Artificial Sequence
<220> FEATURE:
<223> OTHER INFORMATION: Synthetic peptide

<400> SEQUENCE: 3

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Trp Thr Gly Arg Thr Asp Ala Phe Asp Ile Trp Gly Gln Gly
            100                 105                 110

Thr Met Val Thr Val Ser Ser
        115

<210> SEQ ID NO 4
<211> LENGTH: 112
<212> TYPE: PRT
<213> ORGANISM: Artificial Sequence
<220> FEATURE:
<223> OTHER INFORMATION: Synthetic peptide

<400> SEQUENCE: 4

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

```
Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro Leu Thr Phe Gly Gln Gly Thr Lys Val Glu Ile Lys
            100                 105                 110
```

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide

<400> SEQUENCE: 5

```
Ser Ser Asn Trp Trp Ser
1               5
```

<210> SEQ ID NO 6
<211> LENGTH: 16
<212> TYPE: PRT
<213> ORGANISM: Artificial Sequence
<220> FEATURE:
<223> OTHER INFORMATION: Synthetic peptide

<400> SEQUENCE: 6

```
Glu Ile Tyr His Ser Gly Ser Thr Asn Tyr Asn Pro Ser Leu Lys Ser
1               5                   10                  15
```

<210> SEQ ID NO 7
<211> LENGTH: 10
<212> TYPE: PRT
<213> ORGANISM: Artificial Sequence
<220> FEATURE:
<223> OTHER INFORMATION: Synthetic peptide

<400> SEQUENCE: 7

```
Trp Thr Gly Arg Thr Asp Ala Phe Asp Ile
1               5                   10
```

<210> SEQ ID NO 8
<211> LENGTH: 16
<212> TYPE: PRT
<213> ORGANISM: Artificial Sequence
<220> FEATURE:
<223> OTHER INFORMATION: Synthetic peptide

<400> SEQUENCE: 8

```
Arg Ser Ser Gln Ser Leu Leu His Ser Asn Gly Tyr Asn Tyr Leu Asp
1               5                   10                  15
```

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide

<400> SEQUENCE: 9

```
Leu Gly Ser Asn Arg Ala Ser
```

```
<210> SEQ ID NO 10
<211> LENGTH: 9
<212> TYPE: PRT
<213> ORGANISM: Artificial Sequence
<220> FEATURE:
<223> OTHER INFORMATION: Synthetic peptide

<400> SEQUENCE: 10

Met Gln Gly Thr His Trp Pro Leu Thr
1               5
```